DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 7, 1972

896 O.G. 17

T896,008
ESTERS OF 4-METHYLCYCLOHEXANE-METHANOL

David L. Valentine, 4508 Chickasaw Road, Kingsport, Tenn. 37664

Filed Oct. 5, 1970, Ser. No. 78,297
**Int. Cl. C07c *69/80***
U.S. Cl. 260—475 R
No Drawing. 15 Pages Specification

Esters of 4-methylcyclohexanemethanol are useful as plasticizers for vinyl polymers. The esters may be synthesized from 4-methylcyclohexanemethanol alone or in combination with other alicyclic or aliphatic alcohols, and dicarboxylic acids or anhydrides thereof.